US011576733B2

(12) United States Patent
Anglese

(10) Patent No.: US 11,576,733 B2
(45) Date of Patent: Feb. 14, 2023

(54) ROBOTIC SURGICAL ASSEMBLIES INCLUDING ELECTROSURGICAL INSTRUMENTS HAVING ARTICULATABLE WRIST ASSEMBLIES

(71) Applicant: COVIDIEN LP, Mansfield, MA (US)

(72) Inventor: Kurt J. Anglese, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 809 days.

(21) Appl. No.: 16/268,585

(22) Filed: Feb. 6, 2019

(65) Prior Publication Data
US 2020/0246086 A1    Aug. 6, 2020

(51) Int. Cl.
A61B 34/30 (2016.01)
A61B 34/35 (2016.01)
A61B 18/14 (2006.01)
A61B 18/18 (2006.01)
A61B 17/00 (2006.01)

(52) U.S. Cl.
CPC .......... *A61B 34/30* (2016.02); *A61B 18/1442* (2013.01); *A61B 18/1815* (2013.01); *A61B 34/35* (2016.02); *A61B 2017/00477* (2013.01); *A61B 2034/305* (2016.02)

(58) Field of Classification Search
CPC ..... A61B 34/30; A61B 34/35; A61B 18/1442; A61B 18/1815; A61B 2017/00477
See application file for complete search history.

(56) References Cited

U.S. PATENT DOCUMENTS

| 4,815,911 A | 3/1989 | Bengtsson et al. |
| 6,038,817 A | 3/2000 | Scheck et al. |
| 6,132,368 A | 10/2000 | Cooper |
| 6,206,903 B1 | 3/2001 | Ramans |
| 6,245,594 B1 | 6/2001 | Wu et al. |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |

(Continued)

FOREIGN PATENT DOCUMENTS

| CN | 105328710 B | 3/2017 |
| DE | 102008035196 A1 | 2/2010 |

(Continued)

OTHER PUBLICATIONS

European Search Report dated Jul. 10, 2020, corresponding to counterpart European Application No. 20155537.2; 7 pages.

*Primary Examiner* — Michael F Peffley
*Assistant Examiner* — Bo Ouyang
(74) *Attorney, Agent, or Firm* — Carter, DeLuca & Farrell LLP

(57) ABSTRACT

An electrosurgical instrument for use in a robotic surgical system includes an electrosurgical end effector, a housing configured to be operably coupled to an instrument drive unit, a shaft extending distally from the housing, and a wrist assembly coupled to a distal end portion of the shaft. The wrist assembly includes a first pivot member and a second pivot member having a proximal end portion movably coupled to the first pivot member, and a distal end portion configured to be coupled to the end effector. The first pivot member has a pair of first and second distally-extending arms each defining a first groove configured to receive and guide a cable.

19 Claims, 3 Drawing Sheets

(56) References Cited

U.S. PATENT DOCUMENTS

| | | |
|---|---|---|
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,171,279 B2 | 1/2007 | Buckingham et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 3,002,464 A1 | 8/2011 | Grasser et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,245,594 B2 * | 8/2012 | Rogers .................. A61B 34/71 74/490.06 |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |

(56) References Cited

U.S. PATENT DOCUMENTS

| | | |
|---|---|---|
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |

(56) References Cited

U.S. PATENT DOCUMENTS

| | | | |
|---|---|---|---|
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 2006/0199999 | A1* | 9/2006 | Ikeda ............... A61B 1/00149 600/141 |
| 2008/0119870 | A1* | 5/2008 | Williams ............... A61B 34/37 606/130 |

FOREIGN PATENT DOCUMENTS

| | | |
|---|---|---|
| DE | 202012004601 U1 | 6/2012 |
| EP | 3321045 A1 | 5/2018 |
| KR | 20160095795 A | 8/2016 |
| WO | 2012043463 A1 | 4/2012 |

\* cited by examiner

ROBOTIC SURGICAL ASSEMBLIES INCLUDING ELECTROSURGICAL INSTRUMENTS HAVING ARTICULATABLE WRIST ASSEMBLIES

BACKGROUND

Robotic surgical systems have been used in minimally invasive medical procedures. Some robotic surgical systems include a console supporting a surgical robotic arm and a surgical instrument or at least one end effector (e.g., forceps or a grasping tool) mounted to the robotic arm. The robotic arm provides mechanical power to the surgical instrument for its operation and movement. Each robotic arm may include an instrument drive unit that is operatively connected to the surgical instrument.

Manually-operated surgical instruments often include a handle assembly for actuating the functions of the surgical instrument. However, when using a robotic surgical system, typically there is no handle assembly present to carry out the functions of the end effector. Accordingly, to use each unique surgical instrument with a robotic surgical system, the selected surgical instrument may require certain modifications so that the surgical instrument is adapted for use with the robotic surgical system.

SUMMARY

In accordance with an aspect of the present disclosure, an actuation mechanism for actuating an electrosurgical end effector is provided and includes a housing, a shaft extending distally from the housing, and a wrist assembly coupled to a distal end portion of the shaft. The wrist assembly includes a first pivot member and a second pivot member. The first pivot member has a pair of first and second distally-extending arms each defining a groove configured to receive and guide a cable. The second pivot member has a proximal end portion movably coupled to the first pivot member, and a distal end portion configured to couple to an end effector.

In aspects, the groove of each of the first and second arms may have a curved distal section.

In some aspects, the groove of each of the first and second arms may have a linear proximal section.

In further aspects, the curved distal section of the groove of each of the first and second arms may extend along both opposing sides of the respective first and second arms.

In other aspects, the first and second arms may each have a curved distal end portion. The curved distal section of the groove of each of the first and second arms may extend along the curved distal end portion.

In aspects, the wrist assembly may include a coupling member disposed between and movably coupling the first and second pivot members.

In some aspects, the first pivot member may have a proximal end portion defining a channel for accommodating the cable. The channel may be aligned with the groove of one of the first or second arms.

In further aspects, the first and second arms of the first pivot member may be pivotably coupled to the proximal end portion of the coupling member.

In other aspects, the first pivot member may have first and second bosses extending laterally outward from the respective first and second arms. The first and second bosses may pivotably couple the coupling member to the first pivot member.

In aspects, the coupling member may be pivotable relative to the first pivot member about a first pivot axis to adjust one of a pitch or yaw of the end effector, and the second pivot member may be pivotable relative to the coupling member about a second pivot axis to adjust the other of the patch or yaw of the end effector.

In some aspects, the proximal end portion of the first pivot member may define a plurality of channels each for accommodating a respective cable of a plurality of cables, the coupling member may define a plurality of passageways for accommodating the respective cable, and the second pivot member may have a distal end portion defining a plurality of channels for accommodating the respective cable.

In further aspects, the second pivot member may have a pair of first and second proximally-extending arms each defining a first groove configured to receive and guide a cable.

In another aspect of the present disclosure, an electrosurgical instrument for use in a robotic surgical system is provided and includes an end effector and an actuation mechanism. The actuation mechanism includes a housing configured to be operably coupled to an instrument drive unit, a shaft extending distally from the housing, and a wrist assembly coupled to a distal end portion of the shaft. The wrist assembly includes a first pivot member and a second pivot member. The first pivot member has a pair of first and second distally-extending arms each defining a first groove configured to receive and guide a cable. The second pivot member has a proximal end portion movably coupled to the first pivot member, and a distal end portion configured to couple to the end effector.

In yet another aspect of the present disclosure, a wrist assembly for coupling an end effector and a shaft of an electrosurgical instrument is provided and includes a first pivot member and a second pivot member. The first pivot member has a pair of first and second distally-extending arms each defining a first groove configured to receive and guide a cable. The second pivot member has a proximal end portion movably coupled to the first pivot member, and a distal end portion configured to couple to the end effector.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
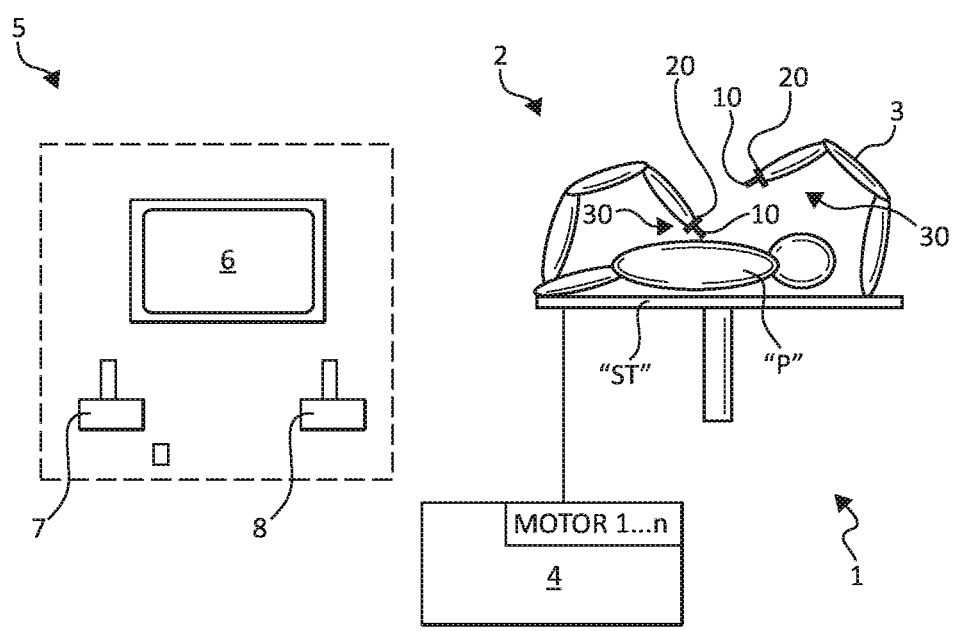
FIG. 1 is a schematic illustration of a robotic surgical system including a robotic surgical assembly in accordance with the present disclosure.

Embodiments of the presently disclosed robotic surgical system including an actuation mechanism for actuating an electrosurgical end effector and methods thereof are described in detail with reference to the drawings, in which like reference numerals designate identical or corresponding elements in each of the several views. As used herein the term "distal" refers to that portion of the robotic surgical system, actuation mechanism, electrosurgical end effector, or component thereof that is further from the user, while the term "proximal" refers to that portion of the robotic surgical system, actuation mechanism, electrosurgical end effector, or component thereof that is closer to the user.

Figure 2:
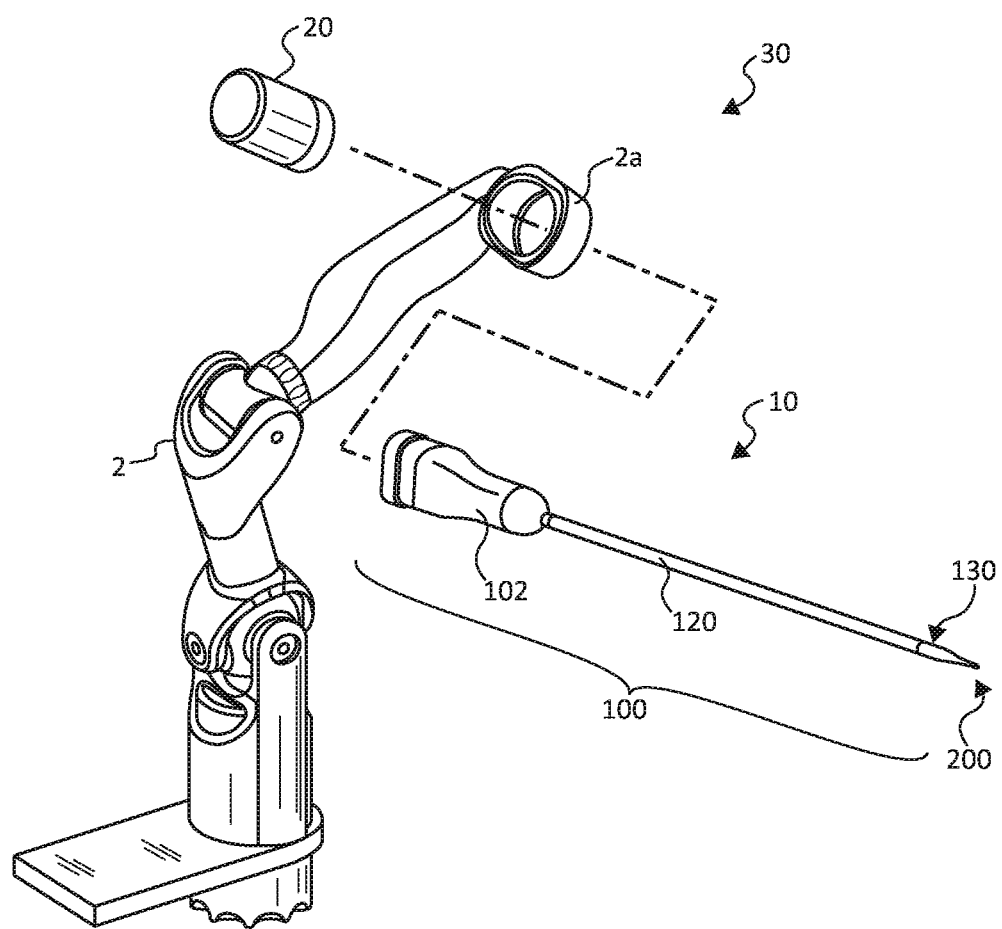
FIG. 2 is a perspective view of a surgical robotic arm of the robotic surgical assembly of FIG. 1 illustrating an electrosurgical instrument and an instrument drive unit being coupled to the surgical robotic arm.

Referring initially to FIGS. 1 and 2, a robotic surgical system 1 is shown and generally includes a plurality of surgical robotic arms 2, 3 each having an electrosurgical instrument 10 removably coupled thereto; a control device 4 (e.g., a computer); and an operating console 5 coupled with the control device 4.

With continued reference to FIG. 1, the operating console 5 includes a display device 6, which is set up to display two-dimensional and three-dimensional images; and manual input devices 7, 8 that serve to enable a user (e.g., a surgeon) to telemanipulate robotic arms 2, 3, as known in principle to a person skilled in the art. Each of the robotic arms 2, 3 may include a plurality of members that are interconnected by joints. The robotic arms 2, 3 may be driven by electric drives (not shown) that are connected to the control device 4. The control device 4 is set up to execute a computer program to activate the electric drives in such a way that the robotic arms 2, 3, their instrument drive units 20, and thus the electrosurgical instrument 10 execute a movement in accordance with a movement of the manual input devices 7, 8. The control device 4 may also be set up in such a way that it regulates the movement of the robotic arms 2, 3 and/or of the electric drives.

The robotic surgical system 1 is configured for minimally invasive treatment of a patient "P" lying on a surgical table "ST" using a surgical instrument (e.g., electrosurgical instrument 10) coupled to the robotic surgical system 1. In some embodiments of the disclosure, the robotic surgical system 1 may include more than two robotic arms that are likewise coupled to the control device 4 and telemanipulatable by the operating console 5. A surgical instrument (e.g., electrosurgical surgical instrument 10) may also be attached to the additional robotic arm(s).

The electrosurgical instrument 10 includes an end effector 200 (FIG. 2) for electrosurgically treating tissue. The control device 4 may control a plurality of motors (Motor 1 . . . n) with each motor configured to drive a relative rotation of drive members of an actuation mechanism 100 (FIG. 2) of the electrosurgical instrument 10 to effect operation and/or movement of the end effector 200 of the electrosurgical instrument 10. It is contemplated that the control device 4 coordinates the activation of the various motors (Motor 1 . . . n) to coordinate a clockwise or counter-clockwise rotation of drive members (not shown) of the instrument drive unit 20 in order to coordinate an operation and/or movement of the end effector 200. In embodiments, each motor can be configured to actuate a drive rod or a lever arm to effect operation and/or movement of the end effector 200 of the electrosurgical instrument 10.

For a detailed description of the construction and operation of a robotic surgical system, reference may be made to U.S. Pat. No. 8,828,023, filed on Nov. 3, 2011, entitled "Medical Workstation," the entire contents of which are incorporated herein by reference.

With specific reference to FIG. 2, the robotic surgical system 1 includes a surgical assembly 30, which includes the robotic arm 2, the electrosurgical instrument 10 coupled to the robotic arm 2, and the instrument drive unit 20 configured to operably couple to the electrosurgical instrument 10. The instrument drive unit 20 is configured for powering the electrosurgical instrument 10. The instrument drive unit 20 transfers power and actuation forces from its motors (not shown) to the actuation mechanism 100 of the electrosurgical instrument 10 to ultimately drive movement of components of the end effector 200, for example, a movement of a knife blade (not explicitly shown) for cutting tissue and a closing and opening of jaw members of the end effector 200 for grasping tissue. An electrosurgical generator (not shown) may be separate or incorporated into the instrument drive unit 20 and coupled, via wires, to the end effector 200 to transmit electrosurgical energy (e.g., RF, microwave, etc.) to tissue sealing plates (not shown) of the jaw members.

The electrosurgical instrument 10 generally includes the actuation mechanism 100, which is configured to be engaged with the instrument drive unit 20 and the end effector 200. The actuation mechanism 100 includes a housing 102 and a shaft 120 extending distally from within the housing 102. The housing 102 is configured to hook, latch, or otherwise attach to a surface of the robotic arm 2, e.g., the distal end 2a of the robotic arm 2, to secure the electrosurgical instrument 10 to the robotic arm 2. In embodiments, the housing 102 may be attached to the surgical robotic arm 2 via various fastening engagements, such as, for example, clips, latches, friction fit engagement, buttons, a variety of fasteners, and/or a bayonet-type connection. The housing 102 houses a gearbox (not explicitly shown) that interfaces with the instrument drive unit 20. The gearbox translates the motion and torques of the motors of the instrument drive unit 20 into the motion necessary to articulate a wrist assembly 130 of the electrosurgical instrument 10, open and close the jaw members of the end effector 200, and deploy and retract a knife blade to cut tissue grasped between the jaw members of the end effector 200.

Figure 3B:
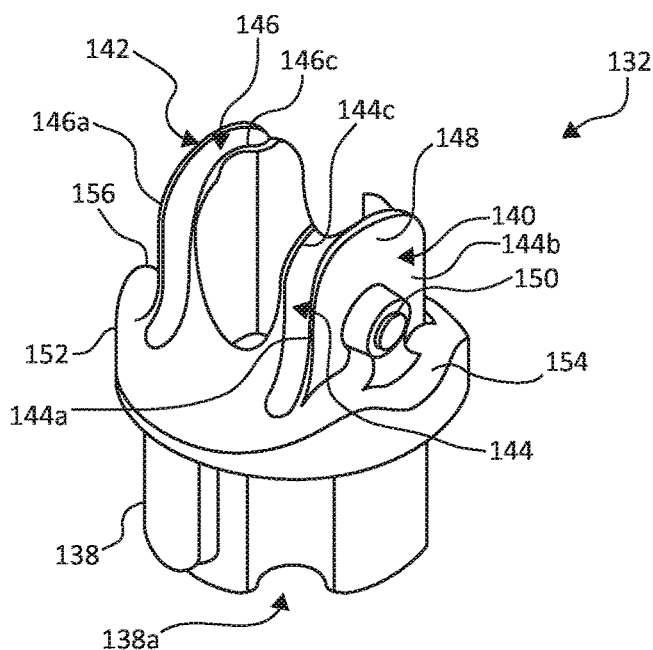
FIG. 3B is an enlarged, perspective view of a pivot member of the wrist assembly shown in FIG. 3A.
Figure 3C:
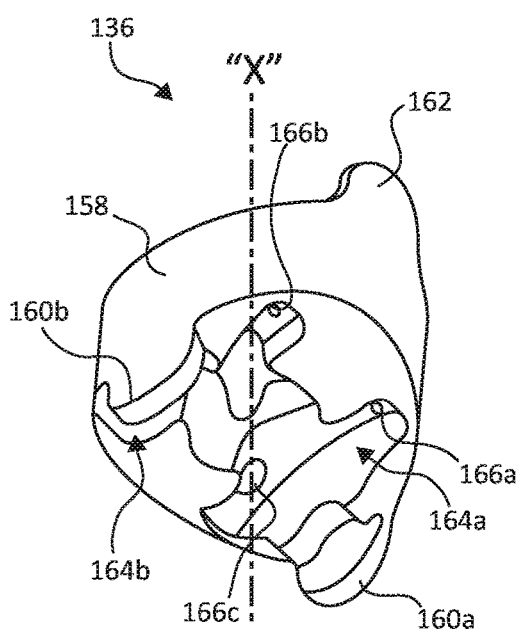
FIG. 3C is an enlarged, perspective view of a coupling member of the wrist assembly of FIG. 3A.
Figure 3A:
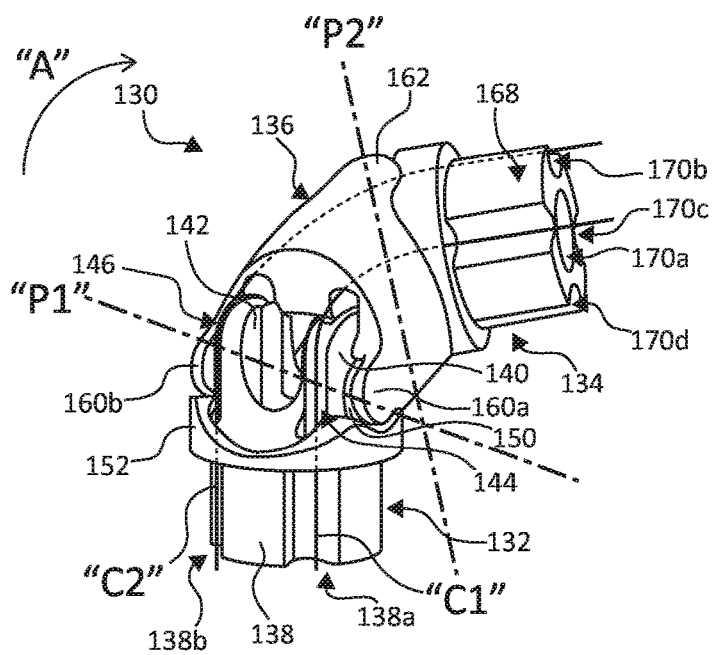
FIG. 3A is an enlarged, perspective view of a wrist assembly of the electrosurgical instrument shown in FIG. 2.

With reference to FIGS. 3A-3C, the wrist assembly 130 of the electrosurgical instrument 10 operably couples the end effector 200 to a distal end portion of the shaft 120. As will be described, the wrist assembly 130 is configured to affect a pivoting motion of the end effector 200 relative to the shaft 120 to adjust the yaw and/or pitch of the end effector 200 utilizing a series of translatable cables driven by the motors of the instrument drive unit 20. The wrist assembly 130 generally includes a first pivot member 132, a second pivot member 134, and a coupling member 136 disposed between and pivotably coupling the first and second pivot members 132, 134. Since the first and second pivot members 132, 134 include similar or the same elements, only the components of the first pivot member 132 will be described in detail herein.

The first pivot member 132 of the wrist assembly 130 has a proximal end portion 138 configured to be fixedly received in the distal end portion of the shaft 120. In other embodiments, the proximal end portion 138 of the first pivot member 132 may be rotatable about the shaft 120 axis. The outer surface of the proximal end portion 138 has a plurality of longitudinally-extending channels 138a, 138b spaced from one another circumferentially about the proximal end portion 138. The channels 138a, 138b are each configured for slidable receipt of a discrete cable "C1," "C2" of a plurality of cables. While only two channels are explicitly shown, the proximal end portion 138 has four channels. In other embodiments, there may be more or less than four channels.

The first pivot member 132 has a pair of first and second arms 140, 142 extending distally from the proximal end portion 138. The arms 140, 142 are spaced apart and parallel with one another and each defines a respective groove 144, 146 therealong. The grooves 144, 146 are aligned and in communication with the respective channels 138a, 138b of the proximal end portion 138 and configured to receive and guide a respective cable "C1," "C2" from the respective channel 138a, 138b. In aspects, due to the shape of the arms 140, 142, the grooves 144, 146 are configured to act as cams during travel of the cables "C1," "C2" therethrough to route the cable over an appropriate length, such that the cable length is conserved during articulation. Since the first and second arms 140, 142 of the first pivot member 132 have similar or the same features, only the features of the first arm 140 will be described in detail herein.

The groove 144 in the first arm 140 has a first proximal section 144a extending from the first channel 138a on a first side of the first pivot member 132, and a second proximal section 144b extending from a third channel (not explicitly shown) on a second, opposite side of the first pivot member 132. The first and second proximal sections 144a, 144b of the groove 144 have a substantially linear configuration, such that the portions of the cables extending therethrough assume a substantially linear configuration.

The groove 144 of the first arm 140 further includes a curved distal section 144c interconnecting the first and second proximal sections 144a, 144b. The curved distal section 144c of the groove 144 extends along a curved distal end portion 148 of the arm 140. The curved distal section 144c of the groove 144 extends uninterrupted from the first proximal section 144a to the second proximal section 144b, such that at least a portion of the curved distal section 144c of the groove 144 is disposed on both sides of the pivot member 132. In embodiments, a gap may be formed in the curved distal section 144c of the groove 144. As will be described in further detail below, the curved distal section 144c of the groove 144 increases the path of travel of the cable received therein to prevent the cable from developing slack during its distal advancement.

The first and second arms 140, 142 of the first pivot member 132 have respective first and second bosses (only the boss 150 of the first arm 140 is explicitly shown) extending laterally outward therefrom. The first and second bosses 150 are configured to pivotably couple to the coupling member 136 of the wrist assembly 130 to allow for pivoting of the coupling member 136 relative to the first pivot member 132 about a first pivot axis "P1." It is contemplated that the first pivot member 132 may have various hinge mechanisms for pivotably coupling the coupling member 136. The first pivot member 132 has an annular ledge 152 disposed between the proximal end portion 138 and the base of the arms 140, 142. The ledge 152 has a pair of first and second concave depressions 154, 156 disposed adjacent the respective first and second bosses 150.

The coupling member 136 of the wrist assembly 130 is a collar disposed between the first and second pivot members 132, 134 and is configured to pivotably couple the first and second pivot members 132, 134 to one another to allow for articulation of the end effector 200 about the first pivot axis "P1" and a second pivot axis "P2." The coupling member 136 has a central body 158, a first pair of tabs 160a, 160b extending proximally from the central body 158, and a second pair of tabs 162 (only one tab 162 is explicitly shown) extending distally from the central body 158. The proximal tabs 160a, 160b rotatably receive the respective first and second bosses 150 of the first pivot member 132 and are received in the respective first and second depressions 154, 156 formed in the ledge 152 of the first pivot member 132. The first pair of tabs 160a, 160b may attach to the bosses 150 in a snap-fit engagement; however, other fastening arrangements are contemplated. The second pair of tabs 162 of the coupling member 136 pivotably couple to the second pivot member 134 in a similar manner.

The first pair of tabs 160a, 160b and the second pair of tabs 162 of the coupling member 136 are offset from one another about a central longitudinal axis "X" defined by the coupling member 136. As such, the first pivot member 132 is pivotable relative to the coupling member 136 about the first pivot axis "P1," and the second pivot member 134 is pivotable relative to the coupling member 136 about the second pivot axis "P2," whereby the first and second pivot axes "P1" and "P2" are non-parallel (e.g., perpendicular).

The central body 158 of the coupling member 136 has a pair of first and second semi-circular slots 164a, 164b each configured to receive the respective first and second arms 140, 142 of the first pivot member 132. The central body 158 defines a plurality of passageways 166a, 166b, 166c therethrough for accommodating each respective cable of the plurality of cables. While not shown, the central body 158 has another pair of semi-circular slots disposed adjacent the tabs 162 configured for receipt of the first and second arms (not shown) of the second pivot member 134.

The second pivot member 134 of the wrist assembly 130 has a distal end portion 168 that defines a plurality of longitudinally-extending channels 170a, 170b, 170c, 170d for accommodating a respective cable. The distal end portion 168 of the second pivot member 134 is configured to be fixedly received in the end effector 200 (FIG. 2). While not explicitly shown, similar to the first pivot member 132, the second pivot member 134 has a pair of first and second arms that pivotably couple to the second pair of first and second tabs 160 of the coupling member 136. The first and second arms of the second pivot member 134 are offset from the pair of first and second arms 140, 142 of the first pivot member 132 about the central longitudinal axis "X" defined by the coupling member 136. In this way, when the wrist assembly 130 is in a straight configuration, the first and second arms 140, 142 of the first pivot member 132 are interdigitated with the first and second arms of the second pivot member 134.

The plurality of cables "C1," "C2" are routed through the wrist assembly 130 and fixed to a distal edge of the second pivot member 134 or a proximal end of the end effector 200. Accordingly, translation of selected cables pivots the end effector 200 in one of a plurality of directions, as will be described further below. For example, as shown in FIGS. 3A-3C, a first cable "C1" runs from the first channel 138a in the first pivot member 132, to the first proximal section 144a of the groove 144 of the first arm 140 of the first pivot member 132, into the first passageway 166a in the coupling member 136, which directs the cable "C1" toward a corresponding proximal section (not shown) of the groove in the first arm of the second pivot member 134, and into the first channel 170a in the second pivot member 134. By way of another example, a second cable "C2" runs from the second channel 138b in the first pivot member 132, to a first proximal section 146a of the groove 146 of the second arm 142 of the first pivot member 132, into the second passageway 166b in the coupling member 136, which directs the cable "C2" toward a corresponding proximal section (not shown) of the groove in the second arm of the second pivot member 134, and into the second channel 170b in the second pivot member 134.

In operation, to adjust an angle of the end effector 200, for example, a pitch angle in the direction indicated by arrow "A" in FIG. 3A, the first and second cables "C1," "C2" are advanced and the third and fourth cables (not shown) are retracted via an actuation of one or more of the motors in the instrument drive unit 20 (FIG. 2). As the coupling member 136, along with the second pivot member 134 and the attached end effector 200, pivot about the pivot axis "P1" in the direction indicated by arrow "A," the first and second cables "C1," "C2" are maintained in the linear proximal sections 144a, 146a of the grooves 144, 146 of the first and second arms 140, 142 and forced or cammed around the respective curved distal section 144c, 146c of the grooves 144, 146 of the first and second arms 140, 142. By being forced to curve around the grooves 144, 146 in the first and second arms 140, 142 of the first pivot member 132, the overall path taken by the first and second cables "C1," "C2" is lengthened compared to the path taken in the absence of the grooves 144, 146. In the absence of the grooves 144, 146, the first and second cables "C1," "C2" would develop slack as they advance distally. Further, the grooves 144, 146 ensure the magnitude of travel of the pair of advancing cables (e.g., cables "C1," "C2") matches the magnitude of travel of the pair of retracting cables.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An actuation mechanism for actuating an electrosurgical end effector, comprising:
   a housing;
   a shaft extending distally from the housing; and
   a wrist assembly coupled to a distal end portion of the shaft, the wrist assembly including:
      a first pivot member having a pair of first and second distally-extending arms each defining a recessed surface configured to receive and guide a cable, each of the first and second arms having a convexly curved distal end portion defining therein a curved distal section of the recessed surface of each of the first and second arms, wherein the curved distal end portion of each of the first and second arms is non-rotatable relative to the respective first and second arms, wherein the recessed surface of the first arm has a proximal section extending on an axis that is parallel with a longitudinal axis of the first pivot member, the curved distal section of the recessed surface of the first arm extending distally from the proximal section; and
      a second pivot member having a proximal end portion movably coupled to the first pivot member, and a distal end portion configured to couple to an end effector.

2. The actuation mechanism according to claim 1, wherein the proximal section is linear.

3. The actuation mechanism according to claim 1, wherein the curved distal section of the recessed surface of each of the first and second arms extends along both opposing sides of the respective first and second arms.

4. The actuation mechanism according to claim 1, wherein the wrist assembly includes a coupling member disposed between and movably coupling the first and second pivot members.

5. The actuation mechanism according to claim 4, wherein the first pivot member has a proximal end portion defining a channel for accommodating the cable, the channel aligned with the recessed surface of one of the first or second arms.

6. The actuation mechanism according to claim 4, wherein the first and second arms of the first pivot member are pivotably coupled to the proximal end portion of the coupling member.

7. The actuation mechanism according to claim 4, wherein the first pivot member has first and second bosses extending laterally outward from the respective first and second arms, the first and second bosses pivotably coupling the coupling member to the first pivot member.

8. The actuation mechanism according to claim 4, wherein the coupling member is pivotable relative to the first pivot member about a first pivot axis to adjust one of a pitch or yaw of the end effector, and the second pivot member is pivotable relative to the coupling member about a second pivot axis to adjust the other of the pitch or yaw of the end effector.

9. The actuation mechanism according to claim 4, wherein the proximal end portion of the first pivot member defines a plurality of channels each for accommodating a respective cable of a plurality of cables, the coupling member defining a plurality of passageways for accommodating the respective cable, and the second pivot member having a distal end portion defining a plurality of channels for accommodating the respective cable.

10. The actuation mechanism according to claim 1, wherein the second pivot member has a pair of first and second proximally-extending arms each defining a first groove configured to receive and guide a cable.

11. The actuation mechanism according to claim 1, wherein the curved distal section of the recessed surface of the first arm is aligned with a longitudinal axis defined by the first arm.

12. An electrosurgical instrument for use in a robotic surgical system, the electrosurgical instrument comprising:
   an end effector; and
   an actuation mechanism including:
      a housing configured to be operably coupled to an instrument drive unit;
      a shaft extending distally from the housing; and
      a wrist assembly coupled to a distal end portion of the shaft, the wrist assembly including:
         a first pivot member having a pair of first and second distally-extending arms each defining a first grooved surface configured to receive and guide a cable, the first arm including a pair of parallel, first and second vertical extensions extending distally from a proximal end portion of the first pivot member, the first grooved surface of the first arm being recessed from the first and second vertical extensions and interconnecting the first and second vertical extensions, the first grooved surface of each of the first and second arms having a curved distal section that is aligned with a longitudinal axis defined by the respective first and second arms; and a second pivot member having a proximal end portion movably coupled to the first pivot member, and a distal end portion configured to couple to the end effector.

13. The electrosurgical instrument according to claim 12, wherein the grooved surface of each of the first and second arms has a linear proximal section.

14. The electrosurgical instrument according to claim 12, wherein the curved distal section of the grooved surface of each of the first and second arms extends along both opposing sides of the respective first and second arms.

15. The electrosurgical instrument according to claim 12, wherein the wrist assembly includes a coupling member disposed between and movably coupling the first and second pivot members.

16. The electrosurgical instrument according to claim 12, wherein the curved distal section of the first grooved surface of the first arm is non-rotatable relative to the first arm.

17. A wrist assembly for coupling an end effector and a shaft of an electrosurgical instrument, the wrist assembly comprising:

a first pivot member having a pair of first and second distally-extending arms each defining a first grooved surface configured to receive and guide a cable, the first grooved surface of the first arm spanning a thickness of the first arm, the first grooved surface of each of the first and second arms having a convexly curved distal section that is aligned with a longitudinal axis defined by the respective first and second arms; and a second pivot member having a proximal end portion movably coupled to the first pivot member, and a distal end portion configured to couple to an end effector.

18. The wrist assembly according to claim 17, further comprising a coupling member disposed between and movably coupling the first and second pivot members.

19. The wrist assembly according to claim 17, wherein the curved distal section of the first groove grooved surface of the first arm is non-rotatable relative to the first arm.

\* \* \* \* \*